United States Patent [19]

St. Martin

[11] Patent Number: 5,567,605
[45] Date of Patent: Oct. 22, 1996

[54] ASSAY FOR D-ALLOSE USING A NAD COFACTOR COUPLED D-ALLOSE DEHYDROGENASE

[75] Inventor: Edward J. St. Martin, Libertyville, Ill.

[73] Assignee: UOP, Des Plaines, Ill.

[21] Appl. No.: 342,502

[22] Filed: Nov. 21, 1994

[51] Int. Cl.$^6$ ............... C12Q 1/32; C12Q 1/26; G01N 33/00; G01N 33/48
[52] U.S. Cl. ............... 435/26; 435/25; 435/4; 436/34; 436/63; 436/74; 436/501; 536/1.11
[58] Field of Search ............... 435/26, 25, 4, 435/23, 14, 24, 94; 436/34, 63, 74, 501; 536/1.11

[56] References Cited

U.S. PATENT DOCUMENTS

| | | | |
|---|---|---|---|
| 3,964,974 | 6/1976 | Banauch et al. | 435/4 |
| 4,963,382 | 10/1990 | Arena et al. | 435/4 |
| 5,032,506 | 7/1991 | Palmer et al. | 435/4 |
| 5,302,513 | 4/1994 | Miike et al. | 435/14 |
| 5,310,665 | 5/1994 | Lambeir et al. | 435/26 |
| 5,358,859 | 10/1994 | Wong et al. | 435/4 |

OTHER PUBLICATIONS

Dahms et al, "J. Biological Chem," vol. 247(7), pp. 2222–2227, 1972.
L. N. Gibbins and F. J. Simpson, 1963, *Can. J. Microbiol.*, 9, 769.
R. P. Mortlock, "Catabolism of Unnatural Carbohydrates by Microorganisms," VIII, D-allose, 1976, *Advances Microbial Physiology*, V. 13, 43–45.
N. Sharon and H. Lis, *Scientific American*, Jan., 1993, pp. 82–89.
*Genetic Engineering News*, Jul., 1994, p. 6 et ff.

*Primary Examiner*—John Kight
*Assistant Examiner*—Louise N. Leary
*Attorney, Agent, or Firm*—Thomas K. McBride; Eugene I. Snyder

[57] ABSTRACT

A D-allose specific dehydrogenase has been isolated which can be used with NAD as a cofactor in a sensitive, specific, quantitative assay for D-allose in aqueous media. A qualitative, color-based test for the presence of D-allose results when an election-accepting dye is coupled to NAD.

6 Claims, No Drawings

ASSAY FOR D-ALLOSE USING A NAD COFACTOR COUPLED D-ALLOSE DEHYDROGENASE

This application relates to an assay for D-allose. More particularly it relates to an assay for D-allose based on a newly discovered dehydrogenase which is specific to D-allose as the substrate.

BACKGROUND OF THE INVENTION

D-allose is an uncommon sugar that rarely has been detected in nature. It has been reported to be present in plant glycosides (Guido W. Perold and Peter Beylis, "Metabolites of Proteaceae," VIII *Nature*, Rubropilosin and Pilorut, 1973, *J. Chem. Soc.*, Perkin Trans. 1, (6), 643–9 and G. W. Perold; P. Beylis and A. S. Howard, "Occurrence of D (+)-allose in Nature", 1971, *J. Chem. Soc. D.*, (11), 597) and in the external polysaccharides of a bacterium (Akira Misaki, Yoichi Tsumuraya and Mariko Kakuta, "D-Allose-Containing Polysaccharide from Methanol by Pseudomonas Sp.", 1979, *Carbohydrate Research*, 75, C8-C10 and Toyo-Soda, "Production of an Allose-Containing Polysaccharide by Cultivation of Pseudomonas Viscogena," 1984, U.S. Pat. No. 4,425,431.) It has not been reported to exist free in solution in nature. A bacterium previously has been described that can utilize D-allose as a sole source of carbon and energy for growth. This microbe was found to contain an ATP linked D-allose kinase enzyme activity (L. N. Gibbins and F. J. Simpson, 1963, *Can. J. Microbiol*, 9, 769 and R. P. Mortlock, "Catabolism of Unnatural Carbohydrates by Microorganisms," VIII, D-allose, 1976, *Advances Microbial Physiology*, V. 13, 43–45.) The product D-allose-6-phosphate could be metabolized further by isomerization to a ketose sugar.

D-allose can be synthesized by chemical epimerization of D-glucose. (Blaise J. Arena, Raymond J. Swedo and Bruce E. Firth, "Molybdate-Containing Anion Exchange Resins for Continuous Interconversion of Epimeric Aldoses and Aldose Analogs," 1988, U.S. 88-288375). This epimerization is not specific and is accompanied by formation of D-mannose and D-altrose. Some pentose sugars structurally similar to D-ribose also are formed. The unique structure of D-allose gives it certain special properties; U.S. Pat. No. 4,963,382. D-allose is not readily metabolized by animals and humans and is easily excreted. Although it is very similar to D-glucose in its taste and physical properties it is non-caloric.

In recent years the role of carbohydrates in cell recognition has become established; N. Sharon and H. Lis, *Scientific American*, January, 1993, pp 82–89. With this has come an increasing realization of the potential importance of carbohydrates, either per se or as a discrete portion of a more complex molecule, as pharmacologically active agents. See, for example, Genetic Engineering News, July, 1994, p. 6 et if. An indispensable prerequisite of pharmaceutical testing, of in vivo studies generally, and of manufacturing processes is an accurate, quantitative, highly specific analytical procedure for D-allose, especially in the presence of normal bodily fluids and in the presence of similar carbohydrates, both pentoses and hexoses. This application is directed to just such an analytical procedure.

In particular, we have isolated a fungus which elaborates a dehydrogenase specific to D-allose. Utilization of the dehydrogenase with nicotinamide adenine dinucleotide (NAD) as a cofactor enables the development of both a simple qualitative test for the presence of D-allose as well as a more elaborate quantitative analysis for D-allose which remains specific to the substrate even in the presence of other materials one could expect to be present under typical analytical conditions.

SUMMARY OF THE INVENTION

The purpose of this invention is to develop a simple, accurate, quantitative assay for D-allose in the presence of other sugars and in complex biological samples. An embodiment comprises the NAD cofactor coupled oxidation with a D-allose dehydrogenase isolated from a mutant, NRRL-21341, of *Exophiala pisciphila*. In a more specific embodiment the assay is conducted at a pH of 9. In another embodiment a qualitative, color-based method for the detection of D-allose using the aforementioned D-allose dehydrogenase in combination with an electron accepting dye.

DESCRIPTION OF THE INVENTION

We have screened natural sources for microorganisms that can metabolize D-allose and isolated a fungus that produces a NAD cofactor-coupled D-allose dehydrogenase enzyme. This new enzyme is very sensitive and specific for D-allose as its substrate. The enzyme can thus be used to develop a qualitative and quantitative assay for D-allose. This enzyme assay can be used to detect and measure D-allose levels in the presence of other similar sugars and in complex biological samples such as foods, blood serum, urine and environmental samples.

ISOLATION OF A D-ALLOSE DEHYDROGENASE PRODUCER

Soil and water samples were obtained from several sites and incubated with D-allose in a basic salts solution. The bacterial and fungal cultures were grown aerobically at 30° C. in a rotary incubator at 250 rpm. The basic salts growth medium contained: $Na_2HPO_4$, 16 raM; $KH_2PO_4$, 34 mM; $(NH_4)_2SO_4$, 15 mM; $MgSO_4$, 1 mM; $CaCl_2$, 0.1 mM; $FeSO_4$, 0.01 mM and D-allose, 10 mM. The pH of the medium was 6.5. After growth in liquid, as determined by an increase in optical density, the cultures were streaked out on solid agar media containing D-allose as the growth substrate. Individual isolated colonies of several bacterial and fungal species were selected and their ability to utilize D-allose as a growth substrate was confirmed. After growth on D-allose, the individual cultures were harvested by centrifugation and the cells disrupted using a sonicator. Cell debris was removed by centrifugation and the crude cell extract was assayed for D-allose dehydrogenase enzymatic activity. One fungal culture had an NAD dependent D-allose enzyme activity. The specific activity of the extracts was approximately 0.3 µmole of product per minute per mg of extract protein as measured at 30° C. The enzyme extract did not contain any measurable $NADH_2$ oxidase enzyme activity that could interfere with the assay by lowering the apparent rate of $NADH_2$ formation. The enzyme is expressed only in fungal cells that have been grown using D-allose as substrate. The enzyme was not detected in cells that had been grown on glucose, glycerol, glycine, acetate or casein amino acids. The specific activity of the enzyme was greatest during active vegetative growth and decreased as the cells reached stationary growth phase and began to sporulate. Because the original fungal isolate readily sporulated and produced a black pigment, UV mutagenesis was used to isolate a non-pigmented and bald (lacking aerial spore forming roycelia) mutant that had a diminished rate of sporulation.

FUNGAL CHARACTERIZATION

Colony Characteristics: On ATCC medium 336 (potato dextrose agar), the colony was 22 mm diam. at 20 days with ambient lab temperature, dark olive, velutinus, mounded, with black reverse. On ATCC medium 200 (YM agar), similar to above but colony coloration was more gray. On media designed to enhance sporulation (one half strength V8 agar with carrot stick, one half strength potato carrot agar with onion skin), mycelium sometimes aggregates into ropes and fascicles.

Morphological Characteristics (on above sporulation media): Conidiogenous cells light olive, terminal, lateral or intercalary, averaging approximately 7.5×2.5 µm, but often more subglobose, approximately 3–4×2.5–3.5 µm, often proliferating percurrently, producing subhyaline, oval to elliptical conidia, 5–8(–10)×2.5–3.5 µm. Conidia nonbudding, but occasionally forming secondary conidia.

The foregoing characteristics match description and illustration of *Exophiala pisciphila* McGinnis & Ajello in de Hoog, G. S. 1977. *Rhinocladiella* and allied genera, in: The Black Yeasts and Allied Hypomycetes. Studies in Mycology No. 17. (illustrated).

The character of the enzyme extract was studied to determine its pH dependence, specificity to D-allose, and susceptibility to inhibition or interference by substrates likely to be present under typical analytical conditions.

ACTIVITY CHARACTERIZATION OF D-ALLOSE DEHYDROGENASE

The enzyme assay was performed with a Beckman DU70 recording spectrophotometer using 340 nanometer wavelength light with 20 sec. interval readings for a 10 minute time period. Assays were run in 1 ml cuvettes at a constant temperature of 30° C. The instantaneous reaction rate was measured as the change in optical density per minute; activity was calculated at early reaction times when the changes in optical density were linear with time. The rate of enzyme reaction is directly proportional to the appearance of reduced NAD at 340 nm, because the enzyme oxidizes D-allose and transfers two protons from D-allose to NAD. The extinction coefficient of $NADH_2$ (6.23 OD/1 mM solution) was used to convert the change in optical density per minute to micromoles of product. A standard curve of reaction rate versus substrate concentration was used to determine the D-allose concentration in unknown samples (FIG. 1). The $K_m$ of an enzyme is the concentration of substrate that gives one half maximal reaction rate and is thus a measure of the affinity of the enzyme for this substrate. The $V_{max}$ of an enzyme is the maximum rate of reaction that can be obtained where the substrate concentration is fully saturating the enzyme. The apparent Km for the enzyme with D-allose as substrate was 77 mM (FIG. 2). When an enzyme extract with a $V_{max}$ of 0.5 O.D./min. is used, the assay can easily detect D-allose concentrations from 1 to 100 mM. An internal standard control using a 20 mM addition of D-allose to a duplicate unknown sample was used to determine if the sample interfered with D-allose measurement. If interference was detected, the unknown sample D-allose concentration was corrected for by the percent interference measured in the internal control sample. The rate for 20 mM D-allose alone plus the rate for the unknown alone (usually measured in the range of 1–5 mM) divided by the rate for the unknown plus 20 mM D-allose was used to determine the correction factor.

The spectrophotometric enzyme reactions were performed in a 1 mL cuvette that contained the following.

| REAGENTS | VOLUME UL | FINAL CONCENTRATION |
| --- | --- | --- |
| Glycine-NaOH-2M-pH 9.0 | 600 | 1.2 M |
| NAD 50 mM | 100 | 5 mM |
| Enzyme extract | 200 | — |
| Unknown or water | 100 | — |

Enzymatic activity was found to be dependent upon the amount of cell extract added. The results of Table 1 were obtained at 30° C. using a solution containing 100 mM in D-allose.

TABLE 1

| Enzymatic Activity | |
| --- | --- |
| Enzyme Extract (µL) | Activity (µmole/min) |
| 0 | <0.05 |
| 20 | 0.09 |
| 50 | 0.15 |
| 100 | 0.26 |

The enzyme activity also was shown to be dependent upon the concentration of D-allose present. In this series, a constant amount of enzyme extract was added to D-allose at various concentrations with the results summarized in Table 2.

TABLE 2

| Concentration Dependence of Enzyme Activity | |
| --- | --- |
| D-allose | Activity µmole/min/ml of extract |
| 0 | <0.07 |
| 1 mM | 0.13 |
| 10 mM | 0.80 |
| 100 mM | 3.07 |

The activity of the enzyme extract toward other substrates also was screened, with the result (Table 3) that the dehydrogenase showed an activity quite specific to D-allose. In these experiments 1 mL of a 100 mM solution of various sugars were treated at pH 9.0 and 30° C. with the same dose of enzyme extract.

TABLE 3

| Carbohydrate Specificity of Enzyme Activity. | |
| --- | --- |
| Sugar 100 mM | Activity µmole/min/ml |
| D-allose | 2.93 |
| D-glucose | <0.07 |
| D-mannose | <0.07 |
| D-altrose | <0.07 |
| D-ribose | <0.07 |

The susceptibility of the enzyme to inhibition by related carbohydrates was determined by comparing the activity of extracts reacted with only 5 mM D-allose with the activity of extracts reacted with other carbohydrates at a concentration of 5 mM. As Table 4 shows, no inhibition was observed within experimental error.

TABLE 4

Enzyme Activity as a Function of Added Sugars

| Sugar 5 mM | % Inhibition[a] |
|---|---|
| D-allose | — |
| D-allose + D-glucose | 3 |
| D-allose + D-mannose | (3) |

[a]Interference measured is within sensitivity level of assay and is not significant.

Enzyme activity is very sensitive to pH with a maximum at pH 9.0 and the activity/pH profile showing a steep slope. Because of the steepness of the slope the buffer concentration assumes increased importance in our analytical procedure by ensuring that a minimum pH change occurs during the course of the reaction. This is shown in Tables 5 and 6. Reactions whose results are summarized in these tables were run with a constant amount of enzyme extract and 100 mM D-allose at 30° C.

TABLE 5

Activity-pH Profile

| pH of Assay Buffer | Activity μmole/min/ml |
|---|---|
| 8.0 | <0.05 |
| 8.5 | 0.78 |
| 9.0 | 2.38 |
| 9.0 | 2.31 |
| 9.5 | 0.10 |
| 10.0 | <0.05 |

The foregoing shows that the assay needs to be performed in the pH range of 8.5–9.5, preferably in the narrower range of 8.8–9.2.

TABLE 6

Effect of Buffer Concentration on Activity

| Buffer (molar) | Initial pH | Final pH | Activity μmole/min/ml |
|---|---|---|---|
| 0.2 | 9.0 | 8.5 | 2.35 |
| 0.5 | 9.0 | 8.9 | 2.56 |
| 1.0 | 9.0 | 9.0 | 2.75 |
| 2.0 | 9.0 | 9.0 | 3.13 |

Because the pH changes where the buffer concentration is inadequate to maintain a constant pH the corresponding rate drops as the reaction proceeds, i.e., there is no linear portion of an optical density vs. time plot. In such cases a rate was averaged over initial portions of the reaction to furnish the data above.

It is likely that the dehydrogenase converts allose to allonic acid, as suggested by the following experiments.

ISOLATION OF D-ALLONIC ACID

D-allose is a six carbon aldohexose sugar and is present in solution in the form of a six sided pyranose ring. Oxidation of D-allose by the enzyme D-allose (NAD) dehydrogenase removes two protons and yields the D-allolactone ring structure. Subsequent hydrolysis of the lactone by chemical catalysis at high pH or by an enzymatic hydrolase would yield the free acid D-allonic acid. D-allose was incubated with D-allose dehydrogenase enzyme and NAD. The reaction was monitored by measuring the appearance of reduced NAD in a recording spectrophotometer. After reaction, the sample was analyzed by ion chromatography. An anion exchange column that is designed for separating anions and organic acids detected a new peak in the reaction sample as compared to a zero time control. The new peak eluted near gluconic and marmonic acid controls but was a separate peak. The product of the D-allose dehydrogenase enzyme reaction appears to be the expected D-allonic acid, but an authentic sample of D-allonic acid was not available to confirm the identity of the new organic acid formed. The use of the isolated enzyme or a blocked mutant of the fungal strain may provide a facile method to convert D-allose into the difficult to synthesize D-allonic acid.

The methods developed above can be used to measure the amount of D-allose in complex synthetic mixtures characteristic of its production methods (Table 7) and to measure D-allose in biological fluids (Tables 8 and 9) according to the foregoing procedures described above.

TABLE 7

Measurement of D-allose during Chemical Synthesis

| Times Samples | Interferance Factor | mM Concentration |
|---|---|---|
| 1 | 1.00 | 1.9 |
| 2 | 1.13 | 9.9 |
| 3 | 1.17 | 11.8 |
| 4 | 1.13 | 9.3 |
| 5 | 1.35 | 35.2 |
| 6 | 1.30 | 26.5 |

The measurement of D-allose in blood serum was accompanied by no significant interference.

TABLE 8

D-Allose in Blood Serum

| D-Allose Concentration | Human Serum | % Inhibition[a] |
|---|---|---|
| 10 mM | 20% | 16 |
| 100 mM | 20% | (16) |

[a]Interference measured is within sensitivity level of assay and is not significant.

The measurement of D-allose in rat urine was accompanied by significant interference which could, however, be readily compensated.

TABLE 9

D-Allose in Rat Urine

| Rat Sample # | Interference Factor | mM | Total mg |
|---|---|---|---|
| 1 | 1.23 | 225 | 1,061 |
| 3 | 1.35 | 332 | 849 |
| 20 | 1.52 | 32[a] | 75 |
| 17 | 1.46 | 23[a] | 40 |
| 19 | 1.45 | 342 | 1,121 |
| 12 | 1.42 | 282 | 661 |
| 4 | 1.13 | 7[a] | 27 |
| 21 | 1.15 | 9[a] | 27 |
| 10 | 1.13 | 99 | 349 |

[a]Interference measured is within sensitivity of level of assay and is not significant.

The assay can be coupled with electron accepting dyes to form a visual qualitative D-allose assay. When the reaction described above is run in the presence of phenozine methosulfate and nitro blue tetrazolium using a compatible phosphate buffer at a lower pH of 8.0, the enzyme can detect D-allose in a sample and yields a color change from light pink to dark blue. Control samples without D-allose remain light pink. The nature of the electron-accepting dye is not critical to the success of this qualitative assay; electron-accepting dyes are well known in the biochemical arts and are merely exemplified by the class of tetrazolium salts, one of which is nitro blue tetrazolium.

The visual D-allose assay contained:

TABLE 10

| Reagents | Volume UL | Final Concentration |
|---|---|---|
| $KPO_4$-0.2M-pH 8.0 | 500 | 0.2 M |
| NAD 50 mM | 10 | 0.5 mM |
| Phenozine Methosulfate 3 mM | 10 | 0.03 mM |
| Nitroblue Tetrazolium 1 mM | 100 | 0.1 mM |
| Triton X-100 | 50 | 5% |
| D-allose 1M or water | 330 | — |

What is claimed is:

1. A method of determining the amount of only D-allose present in an aqueous medium, said aqueous medium optionally containing at least one other D-aldohexose, comprising selectively oxidizing said D-allose with a D-allose-specific dehydrogenase elaborated by a strain of *Exophiala pisciphila* in the presence of nicotinamide adenine dinucleotide at a pH between about 8.5 and about 9.5 and at a temperature from about 25° to about 75° C., measuring the formation of the reduced form of nicotinamide adenine dinucleotide ($NADH_2$), and relating the rate of $NADH_2$ formation to D-allose concentration using a standard curve of $NADH_2$ formation rate versus D-allose concentration.

2. The method of claim 1 where the pH is between about 8.8 and about 9.2.

3. The method of claim 1 where the formation of $NADH_2$ is measured in the ultraviolet spectrum at a wavelength of about 340 nm.

4. A qualitative method of determining the presence of D-allose in an aqueous medium comprising oxidizing said D-allose with a D-allose dehydrogenase in the presence of an electron accepting dye at a pH between about 7.5 and about 8.5 and in the temperature range of between about 25° and about 35° C., and determining the color change accompanying reduction of said dye.

5. The method of claim 4 where the dye is a tetrazolium salt.

6. The method of claim 5 where the dye is nitro blue tetrazolium.

* * * * *